US00PP26926P2

(12) United States Plant Patent
Carroll

(10) Patent No.: US PP26,926 P2
(45) Date of Patent: Jul. 12, 2016

(54) ***ILEX* PLANT NAMED 'DAVID CARROLL'**

(50) Latin Name: *Ilex×meserveae*
Varietal Denomination: David Carroll

(71) Applicant: David Carroll, Cochranton, PA (US)

(72) Inventor: David Carroll, Cochranton, PA (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 90 days.

(21) Appl. No.: 14/121,371

(22) Filed: Aug. 26, 2014

(51) Int. Cl.
*A01H 5/12* (2006.01)

(52) U.S. Cl.
USPC ..... Plt./247

(58) Field of Classification Search
USPC ..... Plt./247
See application file for complete search history.

*Primary Examiner* — June Hwu
(74) *Attorney, Agent, or Firm* — C. A. Whealy

(57) ABSTRACT

A new and distinct *Ilex* plant named 'David Carroll', characterized by its compact and rounded plant habit; freely branching habit; dense and bushy growth habit; bright yellow green-colored leaves; and good garden performance and winter hardiness.

2 Drawing Sheets

Botanical designation: *Ilex×meserveae.*
Cultivar denomination: 'DAVID CARROLL'.

BACKGROUND OF THE INVENTION

The present Invention relates to a new and distinct *Ilex* plant, botanically known as *Ilex×meserveae* and hereinafter referred to by the name 'David Carroll'.

The new *Ilex* plant is a naturally-occurring branch mutation of *Ilex×meserveae* 'Blue Princess', disclosed in U.S. Plant Pat. No. 3,675. The new *Ilex* plant was discovered and selected by the Inventor in November, 2003 on a single plant within a population of plants of 'Blue Princess' in a controlled environment in Wayne Township, Pa.

Asexual reproduction of the new *Ilex* plant by hardwood cuttings in Wayne Township, Pa. since December, 2003 has shown that the unique features of the new *Ilex* plant are stable and reproduced true to type in successive generations of asexual reproduction.

SUMMARY OF THE INVENTION

Plants of the new *Ilex* have not been observed under all possible combinations of environmental conditions and cultural practices. The phenotype may vary somewhat with variations in environmental conditions such as temperature and light intensity without, however, any variance in genotype. The following traits have been repeatedly observed and are determined to be the unique characteristics of 'David Carroll' and in combination distinguish 'David Carroll' as a new and distinct *Ilex* plant:

1. Compact and rounded plant habit.
2. Freely branching habit; dense and bushy growth habit.
3. Bright yellow green-colored leaves.
4. Good garden performance and winter hardiness.

Plants of the new *Ilex* differ from plants of the mutation parent, 'Blue Princess', in the following characteristics:

1. Plants of the new *Ilex* are slower-growing than plants of 'Blue Princess'.

2. Plants of the new *Ilex* have bright yellow green-colored leaves whereas plants of 'Blue Princess' have green-colored leaves.

Plants of the new *Ilex* can be compared to the plants of *Ilex×meserveae×Ilex aquifolium* 'Hachfee', disclosed in U.S. Plant Pat. No. 14,310. In side-by-side comparisons plants of the new *Ilex* differed from plants of 'Hachfee' in the following characteristics:

1. Plants of the new *Ilex* were shorter than plants of 'Hachfee'.
2. Plants of the new *Ilex* had bright yellow green-colored leaves whereas plants of 'Hachfee' had dark green-colored leaves.

BRIEF DESCRIPTION OF THE PHOTOGRAPHS

The accompanying colored photographs illustrate the overall appearance of the new *Ilex* plant showing the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of typical plants of 'David Carroll'.

The photograph on the second sheet is a close-up view of a typical flowering plant of 'David Carroll'.

DETAILED BOTANICAL DESCRIPTION

Plants used in the aforementioned photographs and following observations and measurements were grown during the winter and spring in two-gallon containers in a polyethylene-covered greenhouse in Grand Haven, Mich. and under cultural practices typical of commercial *Ilex* production. Plants were three years old when the photographs and detailed description were taken. In the following description, color references are made to The Royal Horticultural Society Colour Chart, 1995 Edition, except where general terms of ordinary dictionary significance are used.

Botanical classification: *Ilex×meserveae* 'David Carroll'.

Parentage: Naturally-occurring branch mutation of *Ilex× meserveae* 'Blue Princess', disclosed in U.S. Plant Pat. No. 3,675.

Propagation:

*Type*.—By hardwood cuttings.

*Time to initiate roots, summer*.—About 25 days at temperatures about 26° C.

*Time to initiate roots, summer*.—About 42 days at temperatures about 13° C.

*Time to produce a rooted young plant, summer*.—About 126 days at temperatures about 26° C.

*Root description*.—Thick, fibrous and somewhat fleshy.

*Rooting habit*.—Freely branching; medium density.

Plant description:

*Plant and growth habit*.—Perennial shrub; compact and rounded plant habit; vigorous growth habit.

*Branching habit*.—Freely branching habit; dense and bushy growh habit with about twelve primary lateral branches developing per plant.

*Plant height*.—About 30 cm.

*Plant diameter, area of spread*.—About 27 cm.

*Lateral branch description*.—Length: About 27 cm. Diameter: About 1 cm. Internode length: About 5 mm to 15 mm. Strength: Strong. Texture: Smooth, glabrous. Color, developing: Close to 151B. Color, developed: Close to 200A.

Leaf description:

*Arrangement*.—Alternate, simple.

*Length*.—About 3.5 cm to 4 cm.

*Width*.—About 2.4 cm.

*Shape*.—Ovate.

*Apex*.—Acute.

*Base*.—Obtuse to truncate.

*Margin*.—Serrate with short spines.

*Venation pattern*.—Pinnate.

*Texture, upper and lower surfaces*.—Smooth, glabrous; leathery.

*Color*.—Developing leaves, upper surface: Close to 151C; towards the apex, close to 184A. Developing leaves, lower surface: Close to 151A; towards the apex, close to 176C. Fully expanded leaves, upper surface of upper leaves: Close to 151D and becoming closer to 141B; venation, close to 151B and 141B. Fully expanded leaves, lower surface of upper leaves: Close to 144B; venation, close to 144B. Fully expanded leaves, upper surface of lower (shaded) leaves: Close to 135A; venation, close to 135A and towards the base, close to 144B. Fully expanded leaves, lower surface of lower (shaded) leaves: Close to 143C; venation, close to 144B.

*Petioles*.—Length: About 6 mm. Diameter: About 1 mm. Texture, upper and lower surfaces: Smooth, glabrous. Color, upper and lower surfaces of upper leaves: Close to 145A. Color, upper and lower surfaces of lower (shaded) leaves: Close to 144A.

Flower description:

*Flower appearance and arrangement*.—Single axillary rotate flowers; flowers typically in clusters of two to five per axil; flowers face upright to outwardly.

*Natural flowering season*.—Plants flower in the early spring in Michigan; flowers not persistent.

*Fragrance*.—None detected.

*Flower diameter*.—About 9 mm.

*Flower length* (*height*).—About 4 mm.

*Flower buds*.—Length: About 3 mm. Diameter: About 2 mm. Shape: Spherical to oblong. Color: Close to 157B.

*Petals*.—Quantity and arrangement: About four in a single whorl. Length: About 4 mm. Width: About 3 mm. Shape: Oblong. Apex: Obtuse; cupped upward. Margin: Entire. Texture, upper and lower surfaces: Smooth, glabrous. Color: When opening, upper surface: Close to 155C; apical spot, close to 4C. When opening, lower surface: Close to 155C. Fully opened, upper and lower surfaces: Close to 155C.

*Sepals*.—Quantity and arrangement: About four in a single whorl. Length: About 1 mm. Diameter: About 1 mm. Shape: Obovate. Apex: Acute. Base: Truncate. Margin: Entire. Texture, upper and lower surfaces: Smooth, glabrous. Color, upper and lower surfaces: Close to 145B.

*Peduncles*.—Length: About 4 mm. Diameter: About 1 mm. Strength: Moderately strong. Aspect: Upright to outwardly. Texture: Smooth, glabrous. Color: Close to 145B.

*Reproductive organs*.—Androecium: Quantity per flower: About four. Anther length: Less than 1 mm. Anther shape: Elliptic. Anther color: Close to 155C. Pollen amount: Scarce. Gynoecium: Quantity per flower: One. Pistil length: About 3 mm. Style length: About 3 mm. Style color: Close to 144B. Stigma shape: Rounded. Stigma color: Close to 151A. Ovary color: Close to 151C. Fruits (berries): Length: About 8 mm. Diameter: About 8 mm. Shape: Spherical. Texture: Smooth, glabrous. Color, immature: Close to 150A. Color, mature: Close to 45B. Seeds: Viable seed development has not been observed on plants of the new *Ilex*.

Garden performance: Plants of the new *Ilex* have been observed to have good garden performance and to be tolerant to rain, wind and low temperatures about −15° C.

Pathogen & pest resistance: Plants have not been observed to be resistant to pathogens and pests common to *Ilex* plants.

It is claimed:

1. A new and distinct *Ilex* plant named 'David Carroll' as illustrated and described.

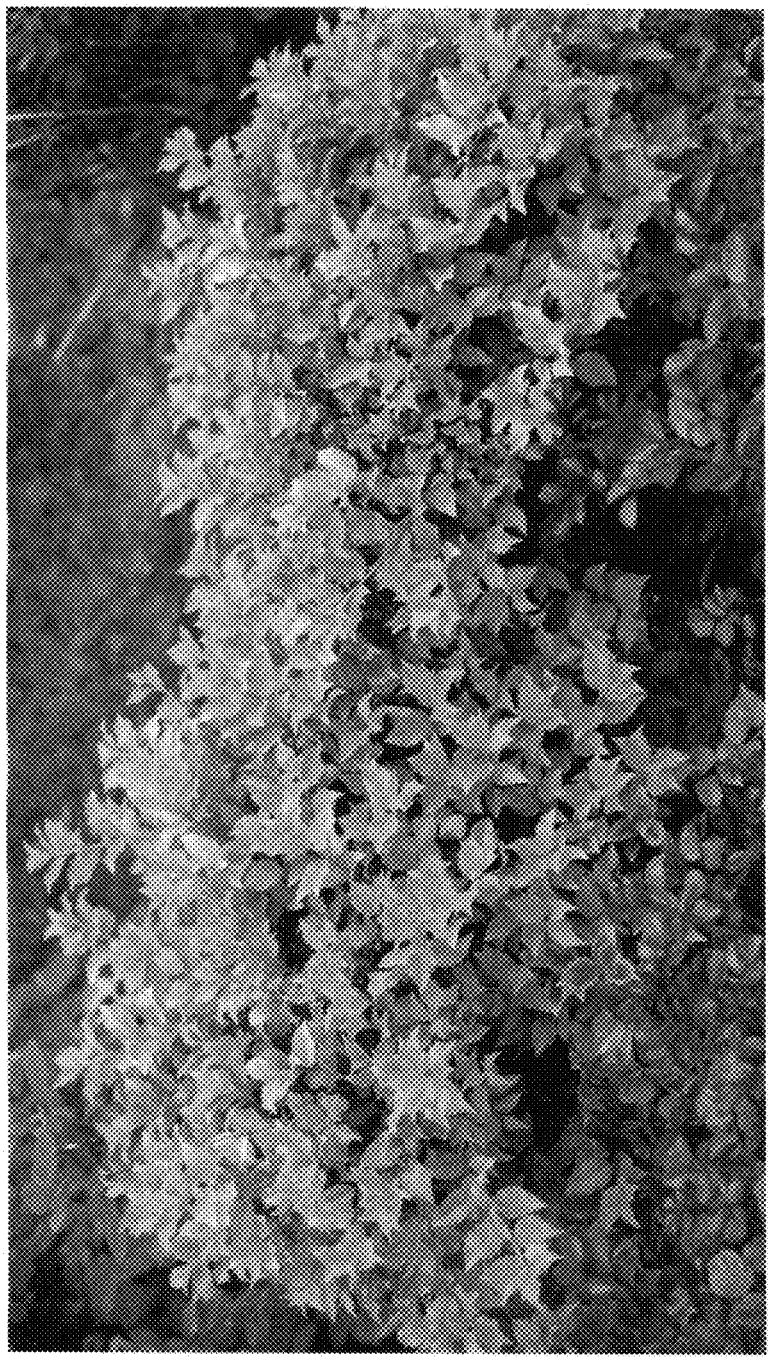

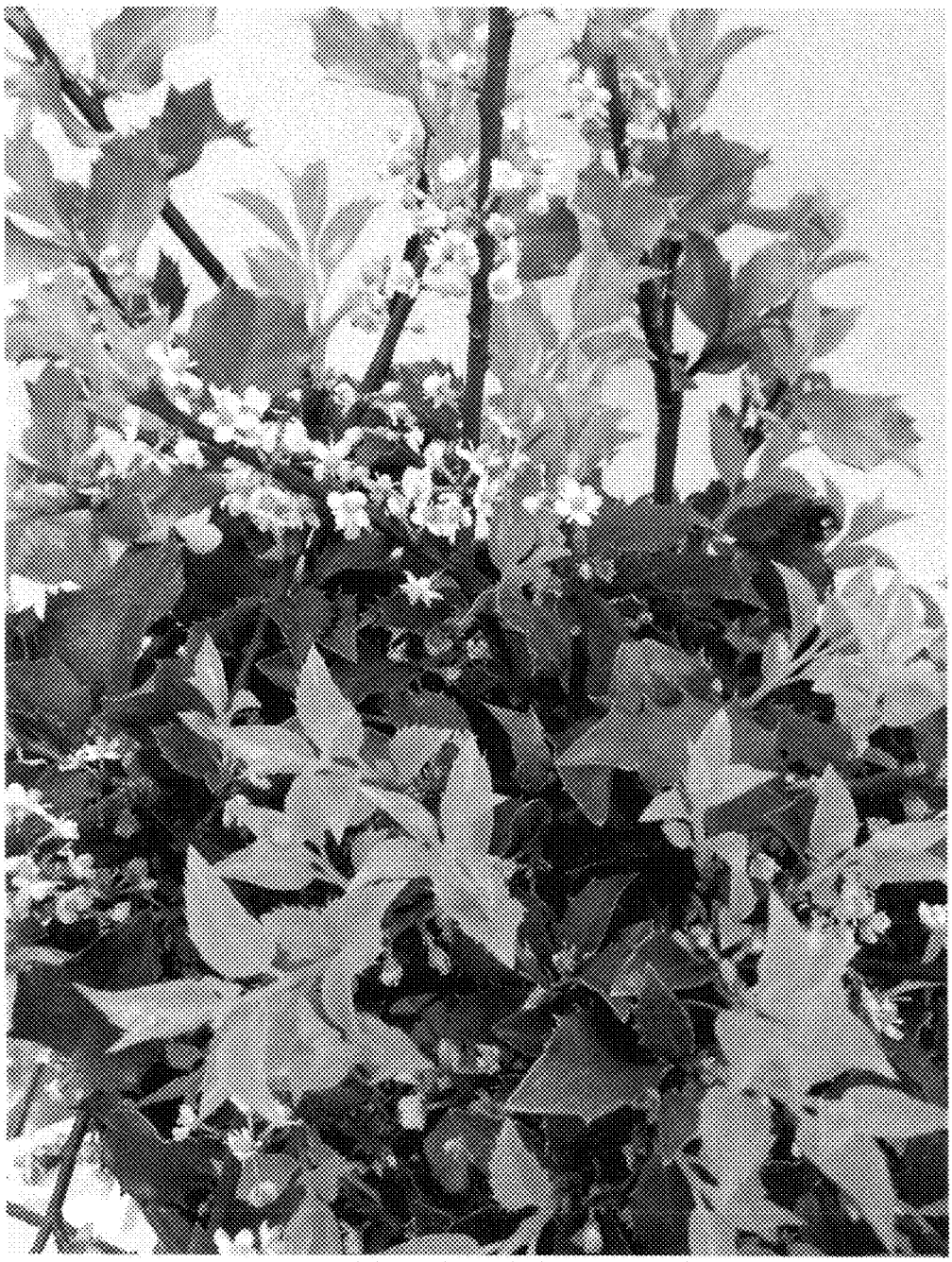

* * * * *